United States Patent [19]

Hillsman

[11] Patent Number: 4,984,158

[45] Date of Patent: Jan. 8, 1991

[54] METERED DOSE INHALER BIOFEEDBACK TRAINING AND EVALUATION SYSTEM

[76] Inventor: Deane Hillsman, 870 El Chorro Way, Sacramento, Calif. 95864

[21] Appl. No.: 257,550

[22] Filed: Oct. 14, 1988

[51] Int. Cl.$^5$ .................... A61B 5/08; G09B 19/00; G06F 15/42
[52] U.S. Cl. .................... 364/413.04; 128/725; 128/905
[58] Field of Search .......... 128/725, 200.14, 200.23, 128/905; 364/413.03, 413.04

[56] References Cited

U.S. PATENT DOCUMENTS

| | | | |
|---|---|---|---|
| 3,991,304 | 11/1976 | Hillsman | 364/413.04 |
| 4,034,743 | 7/1977 | Greenwood et al. | 364/413.03 |
| 4,106,503 | 8/1978 | Rosenthal | 128/200.18 |
| 4,109,656 | 8/1978 | Goethel | 128/203.15 |
| 4,257,415 | 3/1981 | Rubin | 128/200.21 |
| 4,462,398 | 7/1984 | Durkan | 128/200.14 |
| 4,790,305 | 12/1988 | Zoltan et al. | 128/200.23 |
| 4,819,629 | 4/1989 | Jonson | 128/203.22 |

*Primary Examiner*—Jerry Smith
*Assistant Examiner*—David Huntley

[57] ABSTRACT

A visual and auditory biofeedback system instructs patients in proper techniques of inhalation to administer aerosol drugs with Metered Dose Inhaler (MDI) devices. The system displays desired respiratory parameters along with real time performance with computer related technology means. Optimal performance parameters suited to individual patient needs may be generated. Suitable respiratory flow transducer means is used to generate air volume signals in real time, and suitable electronic switching means is used to indicate MDI activation in real time. Optional auditory incentive means are provided. Optional plus and minus error limits of acceptable performance are provided.

The system thus provides visual and auditory biofeedback incentives to improve patient or student performance to mechanical prescription parameters defined by the physician or instructor. Performance deficiency and performance enhancement indicators may be optionally used, both to enhance and to quality control performance. Performance records may be saved by suitable electronic means or hard copy for clinical or research needs.

In the preferred embodiments of the invention, the system may be implemented in either a suitable general purpose digital computer or similar specialized stand-alone computer related devices.

16 Claims, 7 Drawing Sheets

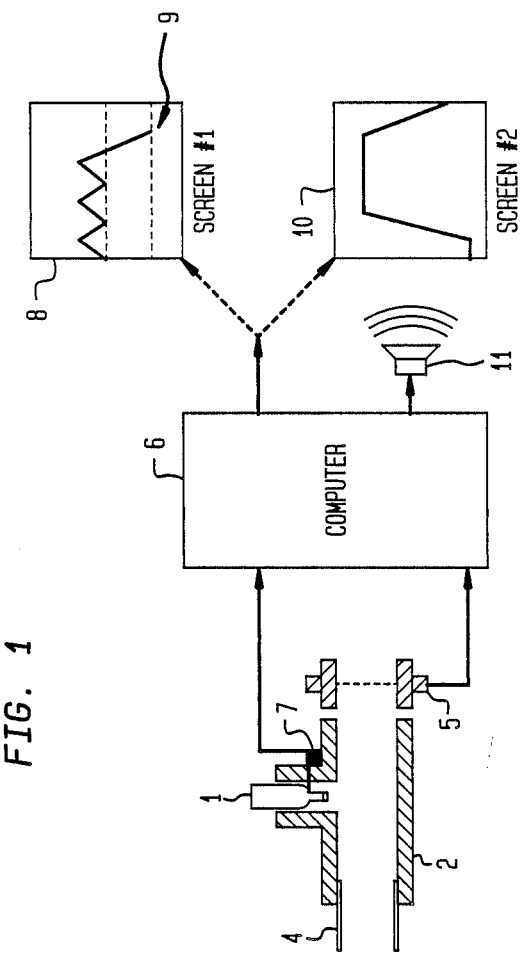
FIG. 1

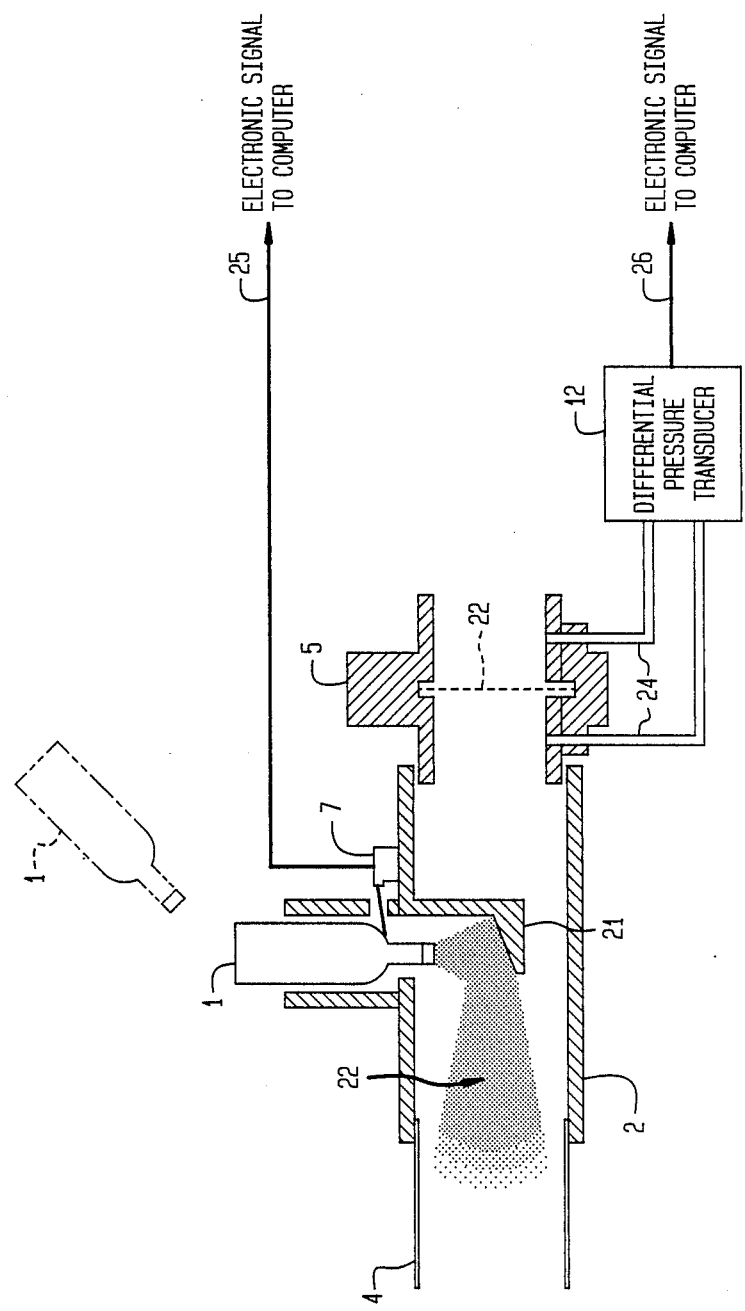

METERED DOSE INHALER BIOFEEDBACK TRAINING AND EVALUATION SYSTEM

BACKGROUND OF THE INVENTION

This invention relates to improved methods and apparatus for display and biofeedback training of respiratory performance in the use of aerosol drug particles and/or mists from Metered Dose Inhaler (MDI) devices. Hillsman is incorporated herein by reference U.S. Pat. No. 3,991,304.

Medical research indicates aerosol administered medications for bronchial therapy in such conditions as asthma, chronic bronchitis and emphysema is generally the preferred dosage technique for reasons of efficacy, reduced side effects and economy. Such particulate drugs are commonly prescribed using MDI type devices. However, in order to achieve these desirable benefits the medication must be inhaled properly for drug delivery to the required site of therapeutic need, namely, the bronchial tubes deep within the lungs. It is well recognized that improper inhalation technique in the use of MDI devices is a serious barrier to effective therapy. Young and elderly patients in particular are subject to improper MDI use, as such patients frequently have problems with learning and coordination of the required technique, as discussed in "Inhalation Aids of Metered Dose Inhalers" (Chang Shim, M.D., CHEST: Vol.91 #3, p315, Mar. 1987).

Patients commonly have difficulty in the use of conventional MDI devices especially in terms of controlling inhalation, and proper activation timing of the MDI delivery system. Typically, among other less common errors, patients will inhale too fast, or in an erratic manner. Frequently they will delay activation of the MDI device until after inspiration has started, and therefore, the crucial initial portion of the inspired breath does not contain medication.

Frequently patients will begin the MDI inspiration breath at an improper level of lung volume, for example, their lungs may already be relatively full of air and therefore a proper large volume of inspired air is impossible. The precise level of desirable initial lung volume is a matter of scientific debate, but most authorities agree it is somewhat less than the so-called Resting Expiratory Level, i.e. the lung volume at the end of normal expiration.

Frequently patients will not inhale the MDI breath to the adequate extent of lung capacity. The desired inspiration volume is also a matter of debate, but most authorities agree it is somewhere just below the so-called Total Lung Capacity, i.e. the maximum possible inspiration lung volume.

Once the proper MDI inspiration breath has been achieved, it is important for the patient to sustain a brief period of breath holding. During this time the medicated mist accumulates moisture, and the aerosol particles become larger and heavier, and therefore are de-entrained or "rain out" from the aerosol suspended state and deposit in the airways. The desired time interval of breath holding is generally thought to be about five to ten seconds. However, this desirable time may be functionally limited, as dictated by individual patient needs and breath holding capabilities.

While it is generally felt the timing of MDI activation should be simultaneous with the beginning of inspiration, there is a minority scientific opinion that questions whether said activation should be a fraction of a second before or after the beginning of inspiration. However, it is understood that these events are substantially concurrent.

It should be apparent from the above, that while the act of using an MDI device may appear simple, it is in fact a complex act, and the proper performance of this technique is crucial to the optimal delivery of drugs to the bronchial airways. Without proper MDI inhalation technique, the patient may in fact derive little or no benefit from this form of drug therapy.

SUMMARY OF THE INVENTION

A unique way to define, teach, and control the use of the Metered Dose Inhaler (MDI) technique using biofeedback means has been found. The system permits the definition of respiratory parameters of lung volumes and air flow, and the proper timing of MDI activation, and breath holding time at end inspiration of the breath containing medication.

This system functions to measure air flow through natural passages, and generate a signal representative of bi-directional air flow. Means is provided to integrate the air flow signal into a volumetric signal, and display same in relation to a time base. The system further provides a circuit to detect the activation of the MDI device and to display this in real time along with the breathing signal. The system permits the visual definition of the volumetric and time parameters, and to display same along with the real time patient performance, as a method of performance training and enhancement with visual biofeedback means and optional auditory feedback. The system further permits the definition of adjustable plus and minus error limits to performance, in relation to the prescribed performance desired, and to detect and display performance deficiencies for technique quality control needs.

Accordingly, it is an object of the present invention to provide a system for sensing and displaying in real time variable analog functions representative of a sensed respiratory biological condition, and hand coordination, for visual comparison with desired predetermined analog functions representative of the state of breathing and the hand activation of the MDI medication delivery device.

This system includes means for real time generation of the analog signal representative of the variable air-flow breathing signal as a waveform and the hand activation of the MDI device by suitable visual display, means to generate desired analog breathing and MDI hand activation patterns, means to provide visual and optional auditory physiologic indications of desired and real time performance, means to generate plus and minus analog percentage parameters of performance adequacy and to indicate and record same, and means to electronically store or hard copy display the desired and actual performance achieved.

In the preferred system, air flow is sensed by means of a differential pressure flow transducer interface device, which sends the differential pressure to a differential pressure transducer sensing device to generate an appropriate electronic signal, which is read into the computer circuitry by an analog to digital converting device. Similarly manual activation of the MDI device is sensed by an electronic microswitch and passed to the computer through the analog to digital converter device. The flow signal is integrated by computational means to a representative volumetric signal, and the MDI activation is converted into an appropriate event marker, and both signals are simultaneously displayed on a computer CRT, LCD or video screen in relationship to a time domain axis. The system likewise permits the system operator to define the various breathing parameters, and the hand activation timing parameter, to derive an optimal MDI user mechanical prescription. The system then displays these desired parameters along with the real time performance.

A further feature of the present invention is means to permit suitable auditory signals of air flow, the time of MDI activation, the time of beginning inspiration of the MDI mist, and the time of breath holding, as well as similar auditory prompts as to when various events in the overall MDI use cycle shall take place. These signals are generated by appropriate computer means and may be activated into the desired sound by either internal computer sound signal means or an external sound generation device. Any suitable prompting means for providing a patient sensed signal may be employed, such as transmitted light, sound, mechanical motion, electrical probe, etc.

Another object of the present invention is the display of patient real time normal breathing patterns prior to the MDI use by means of a separate computer CRT or television screen display, in order to determine a representative resting expiratory level, and to establish same within the system by pattern recognition computational means or optionally by manual adjustment means. Once said resting expiratory level has been determined within the patient and device interactive system, it is then possible to visually display the additional degree of expiration below the resting expiratory level that must be achieved by the patient before activating the second definitive display of proper MDI use.

Another object of the present invention is the setting of analog plus and minus percentage error limits, above and below the desired breathing patterns, with electronic means to detect when patient performance has deviated sufficiently to cross the adjustable degree of error limit. Optionally there is means to make visual and auditory signals of performance deficiencies, and to visually display the percentage error limits along with the desired and real time display analogues.

These and other objects and features of the invention will be seen in the following description and in the drawings.

THE DRAWING

FIG. 1 is a simplified block diagram of the overall system design;

FIG. 3 is a diagram of the electro-mechanical MDI interface;

DESCRIPTION OF PREFERRED EMBODIMENTS

Figure 2:
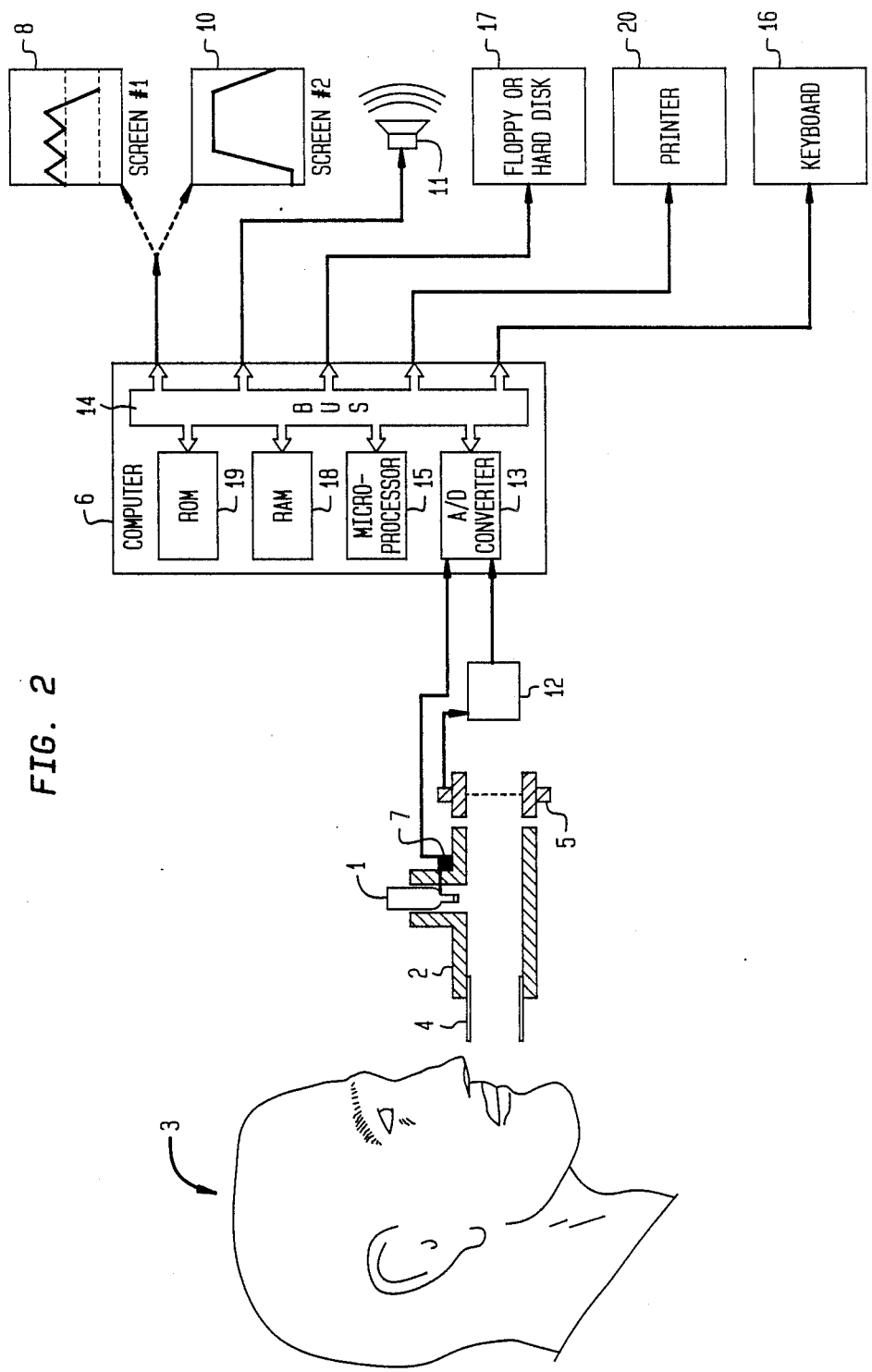
FIG. 2 is a detailed block diagram of the overall system design.

In the following description, metric units are employed unless otherwise stated. Particular attention should is directed toward the treatment of human subjects having pulmonary disorders. The underlying concept relates to the display of optimized breathing patterns in a suitable visual device, and the auditory and visual indication of proper hand activation of the MDI medication device. In the preferred embodiments the patients first see their normal breathing pattern displayed, and the system can then be volume calibrated so the patient's resting expiratory level is synchronized to the training system, and the subject is then visually prompted to exhale below the resting expiratory level to a visually indicated adjustable exhaust lung volume. On achieving this desired exhaust condition lung volume, a second visual display may be activated, this second screen showing the desirable time of MDI activation, inspiration flow rate, inspiration volume, inspiration breath holding time, and expiration flow rates. A blinking video display cursor along these programmed analogues, and optional auditory signals, prompt the patient in proper breathing maneuvers and MDI activation. Preferably, respiratory flow is integrated for display in absolute or relative volumetric units on the vertical ordinate axis, plotted against a time base on the horizontal abscissa axis. Simultaneously the patient's real time breathing performance is displayed by a second solid line signal, and the time of MDI activation by yet another signal, to permit so-called "biofeedback" assistive training to enhance patient performance. In another mode of operation, plus and minus percentage analog error parameters are defined about the optimized breathing patterns, with suitable audio/visual display, alarm, or recording of patient performance for training, quality control, and research purposes.

It is well known in the art, that aerosol or particulate delivery to the lung is a complex maneuver, particularly so in patients with deranged lung function secondary to a variety of disease processes, and in the young and elderly patient with learning and/or coordination difficulties. As such, complex and unique breathing patterns may be needed to solve the mechanical assistive problems in the individual patient, and to effectively train the patient in the desired techniques.

This invention is a breathing training invention specific to breathing maneuvers and technique necessary for proper MDI aerosol medication use, with additional means to indicate and record the proper timing of activation of the standard commercial MDI device, though the inventive concept would not be limited to the use of such MDI devices. The primary device is a sophisticated apparatus that allows for independent adjustment of two sequential computer CRT or TV screens of information. On the first screen, the patient's regular breathing pattern is displayed on a mid-field baseline, and by automated or manually adjustable means a visual indication of the resting expiratory level may be set, in order to synchronize the patient lung volumes with the measuring system. Once set, there is a visual indication of an adjustable lung volume the patient must exhale down to, in order to achieve the proper deflation lung volume to begin the MDI inhalation breath. On achieving said proper deflation lung volume, the system then automatically switches to a second screen of analog information, displaying the specifics of the MDI procedure itself. The second screen begins with the deflated lung volume from the first screen displayed at the bottom of the second screen, for a suitable time interval, for example, 1.0 second. At the end of this time a visual and/or audio prompt signal instructs the patient to activate the MDI device, and simultaneously to begin inspiration. Optionally, the indicated time of MDI activation may be set just before or after the indication of beginning inspiration. The standard inspiration flow patten, displayed by dotted lines, is a linear, constant flow pattern, though optionally curvilinear patterns may be substituted. End inspiration is visually indicated at the top of the screen by a fixed degree of visual analog presentation, and the real end inspiration volume is internally calibrated to reflect the true lung volume, which will be at or near total lung capacity. Thereafter the screen indicates a flat, straight line function of breath holding on deep MDI inspiration, following which the patient exhales, either freely, or optionally in an indicated and controlled manner as with inspiration. A flashing cursor proceeds across the dotted program lines, in the correct time domain relative to volume, and in this manner therefore functions as an instant air flow control device in the indicated time domain. In this manner, the apparently constant visual inspiration slope and volume will in fact properly reflect differing flow rates, depending on the speed of the cursor movement relative to time required for the desired flow rate and the programmed inspiratory lung volume. Similarly, the cursor speed across the fixed length breath holding line will be faster or slower, therefore accurately reflecting the actual time of the breath holding, though the line itself remains identical in length for differing time intervals. Similarly, the expiration flow rate may be controlled if desired. The inspiratory and expiratory airflow into and out of the patient is sensed by suitable transducers, along with the time of MDI activation, and suitably multiplexed into the visual display. Typically, the patient is encouraged to have his real time performance solid line display follow the ideal programmed dotted line display, immediately at the prompting cursor, essentially overlying and obliterating the dotted programmed line. Similarly, the time of MDI activation is visually indicated, to be compared to the desired time of activation. Inadequate patient performance can immediately be seen in a qualitative and quantitative manner in real time, and the patient is therefore encouraged in a positive biofeedback manner to correct his deficient performance. Optionally, for needs of more precise quality control of performance, or for research needs, percentage adjustable plus and minus phantom line error indicating analogues may be placed above and below the regular dotted line programmed prescription analog. Should deficient patient performance result in the patient analog display line crossing a phantom line error limit, audio-visual alarms may be activated and deficient performance recorded in a quantitative and qualitative manner. Optionally individually distinct auditory prompts of beginning MDI inspiration, MDI activation, inspiratory flow, inspiration volume, and breath holding may be employed.

In essence, a mechanical breathing and MDI activation prescription may be derived, similar to the familiar medical drug prescription ordered by a physician. The desirable parameters may then be transferred electronically by such means as conventional Electronically Erasable Read Only Memory (EEROM) from the primary higher technology device into a simple and economical home device for use in the patient's home or similar outside environments to be displayed, for example on a television screen, kinescope, cathode ray tube, liquid crystal display, etc. in an economical manner. This enhances the clinical training program, and assures the patient does not revert to undesirable breathing or MDI activation practices by reinforcing the personally supervised clinical treatment prescription. Similarly, a simpler stand-alone device with standard parameters defined in Read Only Memory (ROM) could be easily implemented.

The patient monitoring and training device described hereinafter is an analog to digital system for achieving real time correlation between a programmed breathing cycle and MDI activation event. This apparatus provides a display of these functions essentially simultaneously in so far as the human observer is able to distinguish. Although time lags may be easily distinguished by electronic means, the visually discernable display is essentially simultaneous with the waveforms being temporally and spatially coordinated.

The circuitry in the block diagram of FIG. 1 shows a simplified schematic of the overall preferred methods and apparatus to input the breathing pattern and MDI activation event into a computer device, and to display breathing performance and MDI performance on the computer CRT or television screen, and to obtain an auditory output of certain key events. The Metered Dose Inhaler (MDI) device 1 is inserted into the MDI Interface device 2. Patient 3 breaths in and out of the MDI Interface 2 through disposable Mouthpiece 4. A Differential Pressure Flow Transducer Interface 5 inputs flow signals to a standard digital Computer 6 such as the IBM Personal Computer, and likewise an Electronic Microswitch 7 sensing MDI 1 manual activation movement and inputs an electronic pulse to Computer 6. Computer 6 integrates the air flow signal into a volumetric signal, which is then displayed on a computer CRT, LCD or television screen in relationship to a time based axis. Initially on Screen #1, 8 patient normal breathing and expiration prior to MDI activation is shown on a mid-field display, which in turn activates Screen #2, 10 which is the MDI definition and prompting display. Sound Generator 11 generates appropriate sounds on command from the Computer 6 device.

The schematic block diagram in FIG. 2 is a more detailed overall description of the system design. The Differential Pressure Flow Interface 5 such as the Fleisch or Hans Rudolph devices, transmits the generated differential pressure to a Differential Pressure Transducer 12 such as the Validyne or Celesco transducers, which generates appropriate electronic signals which are input into Computer 6 by means of an Analog to Digital Converter (A/D) 13. The MDI activation signal from the Microswitch 7 is similarly input to Computer 6 by way of the A/D 13. Internal to the Computer 6 design is electronic architecture known generally as a Bus 14 which shunts electronic control signals within the computer and in and out of various computer ports to external devices under the control of Microprocessor 15 using appropriate computer software instructions. Operator input from Keyboard 16 permits the definition of various breathing patterns and other events. Floppy or Hard Disk 17 contains operational software programs which may be loaded into computer Random Access Memory (RAM) 18 to permit the special programs related to this invention to work the system, and likewise Disk 17 may be used to store data derived from functional use of the system. Alternatively the operational software may be stored in Read Only Memory (ROM) devices to enhance program execution in ROM 19 or even obviate the need for external memory devices such as Disk 17. The functional operational architecture of the device generally revolves about two areas of computer 6 memory under general control of microprocessor 15. For ease of description the first memory means is indicated as ROM 19, which contains the desired breathing performance and other prompting performance auditory and visual analogs and a second memory means indicated as RAM 18, which contains the real time subject performance data. However, this memory area indicated as ROM 19 is the functional equivalent of appropriately partitioned memory within RAM 18, as identical functional optimal parameters may be placed in this partitioned RAM 18 by importing said optimal patterns from floppy or hard disk 17 by way of bus 14, or derived de novo from algorithms calculated subsequent to parameter input from keyboard 16 by way of bus 14. Second memory means always resides within ROM 19, as this memory receives dynamic patient performance data and stores the information in so-called mathematical arrays, for subsequent data manipulation, or display if said digital data is converted to an analog display. Microprocessor 15, which contains a clock or timing device, coordinates all system activities such as correct timing between first memory means ROM 19 and second memory means RAM 18, multiplexing of various input and output signals, and the overall coordination of events, such as computer detecting means, counter means, accumulator means, integrating means, comparator means and resetting means, leading to the auditory and visual scanning beam rectilinear raster coordinated display. Patient performance may likewise be hard copy output to Printer 20. As previously described, output from the operation of the system is displayed on either Screen 8 or Screen 10, and auditory output is indicated by Sound Generator 11.

The diagram in FIG. 3 is a detailed drawing of MDI Interface 2. This device is attached to the patient's mouth by Disposable Mouthpiece 4. When MDI 1 is pressed into the interface by hand activation from the patient, a valve in the MDI is opened briefly, and a metered amount of propellant mist containing dissolved or suspended medication is released, and is impacted on a Baffle 21 to be directed toward the patient as a jet of Mist 22. As the MDI 1 is pushed downward in the process of activation, the shoulder encounters a lever on Microswitch 7 to activate an electronic signal 25 to Computer 6. On the opposite end of the MDI Interface 2 is a Differential Pressure Flow Transducer Interface 5, for example the commercially available Hans Rudolph device Model 4700. A wire mesh Grid 22 produces a bi-directional downstream differential pressure on inspiration and expiration which is sensed by Differential Pressure Ports 24 on each side of the Grid 22, with appropriate hoses to conduct said differential pressures to the Differential Pressure Transducer 12 to generate the appropriate electronic signal 26 for input to the Computer 6.

Figure 4A:
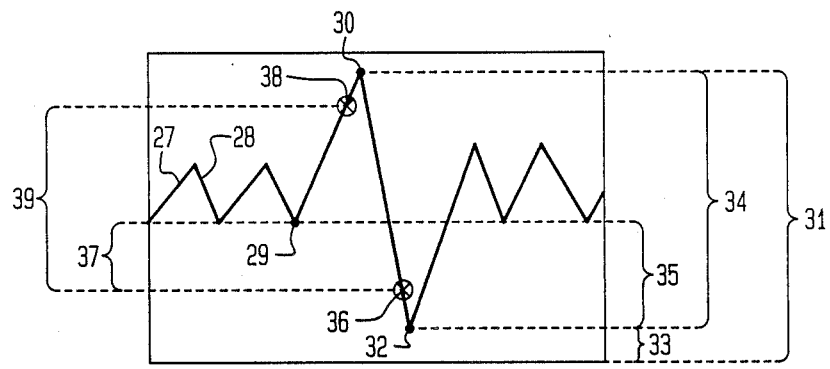
FIG. 4a to 4b are schematic representations of lung volumes and the lung volume settings with this invention.
Figure 4B:
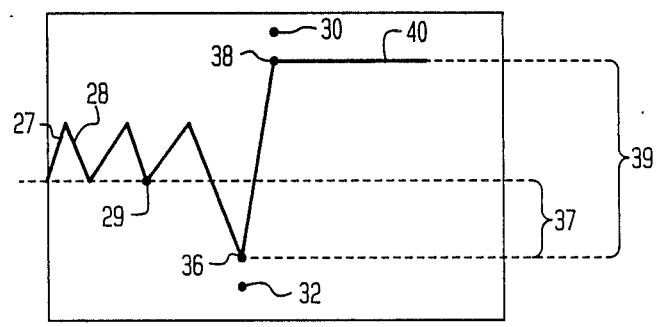

The diagram in FIG. 4a is a standard common graphic representation of human lung volumes, in a manner commonly known to those skilled in the art of respiratory physiology. Inspiration Tidal Volume 27 and Expiration Tidal Volume 28, the volumes of air inspired and expired during normal breathing, are displayed in midfield. The end of expiration, the so-called Resting Expiration Level 29, by convention, is a landmark reference respiratory volume, as normally there is a slight pause at end expiration and the event is easy to recognize. The point of Maximum Inspiration 30 defines the Total Lung Capacity volume 31. The point of Maximum Expiration 32 defines the Residual Volume 33. By convention the volume between Maximum Inspiration 30 and Maximum Expiration 32 is known as the Vital Capacity volume 34. By convention the volume between Resting Expiratory Level 29 and Maximum Expiration 32 is known as the Expiratory Reserve Volume 35. The MDI End Expiration Volume 36 is the volumetric set point above Maximum Expiration 32 and previously determined Residual Volume 33, where MDI activation and the inspiration of medicated mist begins. The MDI End Expiration volume 36 and Resting Expiratory Level 29 defines the MDI Expiration volume 37. The MDI End Inspiration Volume 38 is the volumetric set point below Maximum Inspiration 30 and previously determined Total Lung Capacity 31 where the inspiration of the medicated mist ends, and Breath Holding 40 begins, in FIG. 4b. The MDI End Expiration Volume 36 and MDI End Inspiration Volume 38 defines the MDI Inspiration Volume 39. It should be apparent from these considerations, if the Vital Capacity volume 34 is input to the computer, and likewise the desired volumes above Maximum Expiration 32 and the desired volume below Total Lung Capacity 30, the MDI Inspiration Volume 39 may be easily calculated. Alternatively, if the Residual Volume 33 and Total Lung Capacity 31 are not known, the operator may directly input the MDI Expiration Volume 37 and MDI Inspiration Volume 39. The MDI Inspiration Volume 39 with reference to normal Tidal Volume breathing 27, 28 is shown in conventional graphic representation in FIG. 4b, and further the Breath Hold 40 maneuver volume is depicted. It should be apparent from these considerations, if the patient lung volumes are referenced to the Resting Expiratory Level 29 the actual patient lung volumes will be calibrated and coordinated with the MDI measuring and training system.

Figure 5:
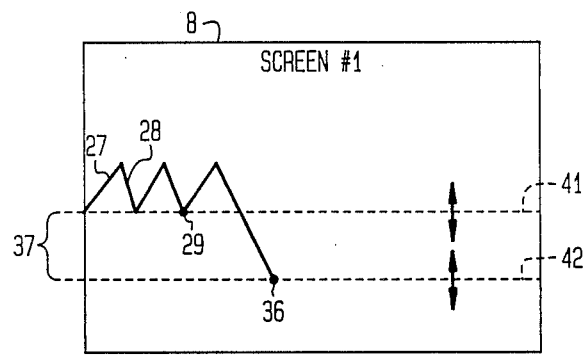
FIG. 5 is a schematic representation of the mid-field visual display of patient normal breathing prior to MDI activation, and the MDI activation expiration volume parameter.

Computer software programmed into RAM 18 and/or ROM 19 now instructs Microprocessor 15 via Bus 14 to generate Screen #1 8 as shown in FIG. 5. The normal Inspiration Tidal Volume 27 and Expiration Tidal Volume 28 is shown in a mid-field display, sweeping across the display from left to right and refreshing at the end of each sweep cycle. Normally the Resting Expiratory Level 29 fluctuates somewhat, but a reasonable resting average level may be readily determined by computer pattern recognition means and averaging techniques. Optionally the Resting Expiratory Level 29 can be visually averaged by the operator, and visually established within computer control by using up and down computer keyboard 16 control keys to move adjustable Resting Expiratory Level (REL) Indicator Line 41 to coincide with the Resting Expiratory Level 29. The MDI Indicating Line 42 will be set a fixed appropriate distance by the calculated or input MDI Expiration Volume 37, and will move up and down in parallel with adjustments to the REL Indicating Line 41. When the operator judges the patient respiration to be suitable stable and the REL Indicating Line 41 accurately established, the patient is then instructed to exhale down to the MDI Indicating Line 42, i.e. the MDI End Expiration Volume 36. When the patient exhales to this point computer means senses and triggers the actual MDI training session by eliminating Screen #1 8 and substituting Screen #2 10.

Figure 6:
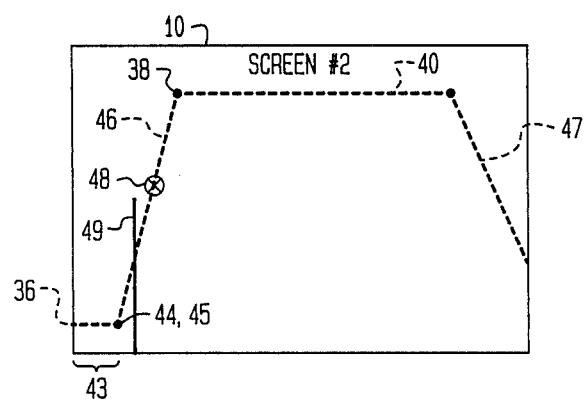
FIG. 6 is a schematic representation of the MDI performance display.
Figure 7A:
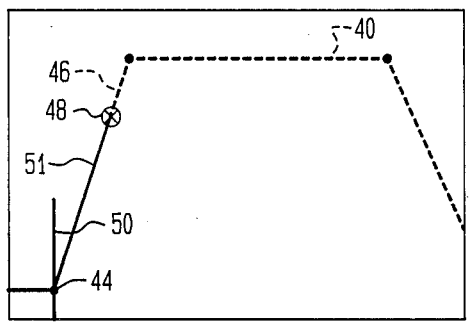
FIG. 7a to 7b are graphic displays of typical satisfactory and unsatisfactory MDI patient performance showing.

The MDI training display on Screen #2 10 is shown in FIG. 6. The patient is presented with a dotted mechanical breathing prescription line with the MDI End Expiration Volume 36 at the lower left corner of the screen, for a standard 1.0 second Expiration Delay 43, MDI Activation point 44, MDI Inspiration Point 45, MDI Inspiration Waveform 46, MDI End Inspiration Volume 38, Breath Hold volume and time 40, and Expiration Waveform 47. Normally the MDI Inspiration Point 45 and MDI Activation Point 44 are identical, and are indicated 1.0 second 43 after the beginning of activation of Screen #2 10. Alternatively the time of MDI activation 44 may be set just before or just after the beginning of MDI inspiration 45. In this case the timing and screen position of the MDI Inspiration Point 45 remains in the standard form as shown, and the MDI Activation Point 44a (not shown) is separately indicated at an appropriate time (and therefore distance) before or after the MDI Inspiration Point 45. A blinking Cursor 48 begins at the left side dotted prompting line and proceeds through the entire sequence of dotted program prescriptions 36, 46, 40 and 47 in the correct time domains relative to each program section. Depending on the volumetric and time considerations, it is apparent the speed of cursor movement in MDI Inspiration Program prescriptions 46 and the MDI Expiration Waveform 47 will vary, depending on the individual need for instant air flow control. Likewise in the Breath Hold 40 section, depending on the time of programmed breath holding, cursor 48 will move at differing rates depending on the programmed time of breath holding. Optionally the program sections 44, 44a, 46, 40 and 47 may have individual auditory prompts to further enhance visual training or to function as an aid to visually handicapped patients. As the patient inhales, breath holds, or exhales he is encouraged to superimpose his solid line real time breathing performance on the dotted program prescriptions, in time with Cursor 48 prompting as shown in FIG. 7a, and therefore to precisely mimic the MDI breathing prescription. Similarly the patient is encouraged to superimpose the MDI Activation signal 49 on the MDI Inspiration/Activation Point 44 or 44a. If either the breathing maneuvers or MDI activation time are not correct, the patient will have an immediate display of deficient performance and therefore a visual biofeedback prompt to correct deficient performance.

Figure 7B:
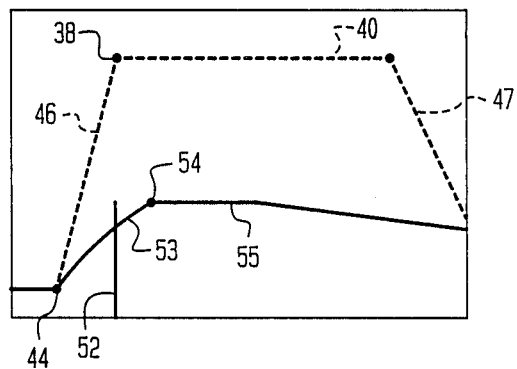

Correct and deficient patient performance is shown in FIG. 7a and 7b. FIG. 7a indicates correct patient performance, with correct MDI Activation 50 superimposed on the MDI Inspiration / Activation Point 44, and correct solid line patient inspiration performance 51 superimposed on the programmed desired inspiration breathing prescription 46 at Cursor 48. FIG. 7b indicates deficient patient performance, with late MDI activation 52 indicated and not superimposed on MDI Activation/Inspiration point 44, and slow inspiration 53 not superimposed on programmed inspiration line 46, and inadequate MDI inspiration volume 54 not superimposed on programmed MDI End Inspiration Volume 38, and short breath holding time 55 indicated in contrast to desired correct Breath Hold Time 40.

Figure 8A:
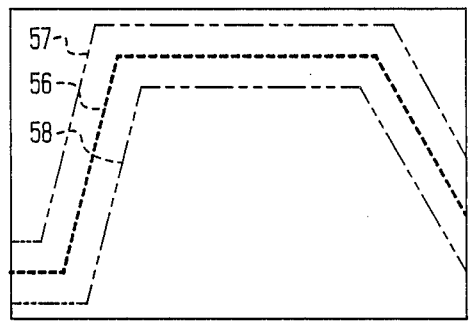
FIG. 8a to 8c is a schematic representation of the phantom line error detection means, with plus and minus error limit phantom lines, and with diagrams indicating of satisfactory and unsatisfactory patient performance showing.
Figure 8B:
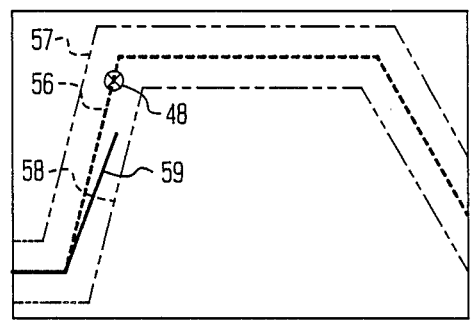
Figure 8C:
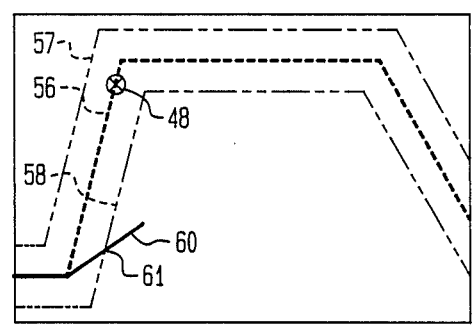

FIG. 8 a, b and c diagrams illustrate the phantom line error detection concept. FIG. 8a shows generally programmed prescription lines 56 and positive percentage phantom error limit line 57 and negative percentage phantom error limit line 58. FIG. 8b shows adequate patient performance, where patient performance line 59, while not precisely superimposed on desired program line 56 does not touch phantom line 58 and therefore will not be detected or otherwise indicated as deficient patient performance. FIG. 8c shows deficient patient performance, with patient performance line 60 deviating from desired program line 56 and touching phantom line 58 at point 61 to activate optional auditory and visual alarms and be recorded as deficient performance.

This invention has been described with computer means as a part of the overall system. The concept may likewise be implemented in a stand-alone device using dedicated microprocessor logic means and dedicated ancillary electronic device means, for example, with all electronic components compiled into a single integrated functional electronic chip device. The scope of this invention therefore is not meant to be limited to required use of a general computer or general micro-computer based device.

While the invention has been explained by particular examples in the specifications and drawing, there is no intent to limit the inventive concept except as set forth in the following claims.

What is claimed is:

1. Inhalation therapy apparatus for enhancing patient performance during inhalation of aerosol treatment materials comprising:
    airflow conduit means for receiving inspiration and expiration air from the patient;
    manually activated means for introducing a metered dose of aerosol treatment material or placebo substitute into the airflow conduit means;
    means for measuring patient inspiration and expiration airflow and generating a first signal representative of said airflow;
    means for determining a cyclic expiration point representative of lung exhaustion and generating a second signal upon lung exhaustion;
    dosage signal means responsive to said second lung exhaustion signal to indicate to the patient to begin an inspiration cycle and substantially simultaneous manual activation of said manually activated means;
    means for indicating completion of air intake in said inspiration cycle and manual activation of said manually activated means; and
    means for indicating to the patient a prescribed inhalation airflow pattern.

2. A training method for teaching inhalation drug administration to a human subject comprising the steps of:
    measuring normal subject respiration in an airflow conduit operatively connected to the subject's respiration passages, an airflow bi-directional flow sensor and an aerosol material supply;
    generating a signal representative of subject normal resting respiratory airflow;
    integrating the airflow signal to provide a real time tidal volume signal;

visually displaying the tidal volume signal in a time axis volumetric display;

determining normal lung expiration level and full normal inspiration volume for at least one subject's resting respiratory cycle;

determining in a subsequent respiration cycle when the subject's lung expiration level is achieved below the predetermined normal resting expiration level;

initiating a dosage cycle by transmitting to the subject a command signal to manually activate flow of aerosol material from the aerosol supply into the airflow conduit, and;

visually displaying to the subject during the dosage cycle a prescribed tidal volume inspiration-expiration flow pattern, thereby permitting controlled introduction of the aerosol material with a predetermined inspiration volume and flow rate and affecting deposition of aerosol material in the subject's lung during the dosing cycle prior to expiration.

3. The method of claim 2 wherein said prescribed inspiration - expiration flow pattern includes a time delay at approximately full inspiration volume prior to expiration.

4. The method of claim 2 wherein normal resting respiration is displayed on first display screen and dosage cycle respiration is displayed on a second screen.

5. The method of claim 2 further including the steps of:

detecting initiation of dosage cycle inspiration and resetting the prescribed tidal volume flow pattern;

comparing the real time tidal volume signal with the the prescribed tidal volume flow pattern correlated with inspiration reset; and visually displaying the real time tidal volume signal and the prescribed tidal volume flow pattern in visually discernable superimposed observation modes.

6. A system for sensing and displaying in real time a variable analog function representative of respiration air flow for visual comparison with a predetermined dosing cycle analog function representative of an optimal prescribed respiration condition, comprising:

means for generating an analog signal representative of the variable analog function;

display means for visual display of said variable analog function and said predetermined dosing cycle analog function, having scanning means with a predetermined frame time, a scanning beam and having a predetermined scan raster and frame;

means for determining a normal expiration volume;

means for generating a prompt signal when said normal expiration volume is exceeded beyond a predetermined volume;

first memory means for storing said predetermined dosage cycle analog function as a waveform;

means for providing and storing digital signals representative of the variable analog function in second memory means;

metered dose cycle initiation means, manually actuated in response to said prompt signal;

manually actuated means for reading out each of said first memory means and second memory means in timed relation to the scan rate of said display means, and;

means for generating a display in said display means when a value read out from either of said first and second memory means corresponds to a current scanned position of said display means.

7. The system of claim 6 wherein each of said first memory means and second memory means comprise digital memories;

said first memory means storing digital sample values of said predetermined analog waveform; and said system further including means for integrating said sensed analog signal and means for generating digital sample values of said integrated signal at a time rate synchronized with the line rate of scan of said display means.

8. The system of claim 7 further comprising:

multiplexing means for storing successive digital sample values in corresponding successive storage positions of said second memory means at a first rate related to a respiration time cycle of said variable analog function and for reading out digital values in alternating succession from each of said first and second memory means at a second rate related to the rate of scanning each successive line of said display means;

counter means for accumulating a count corresponding to the number of lines scanned in a given raster scan of said display means; and comparator means for comparing the digital value read from either of said first and second memories under control of said multiplexing means with the line count of said line counter means for producing a video display output when said digital line count corresponds to said digital value read from said first or second memory means.

9. The system of claim 8 comprising:

a first digital-to-analog converter for converting the digital value of the predetermined analog waveform read from said first memory means to a corresponding analog signal;

a second digital-to-analog converter for converting the digital sample values of said variable analog waveform read from said second memory means; and first signal comparator means for producing an output representing a predetermined difference between the said analog outputs of said first and second digital-to-analog converters.

10. The system of claim 6 wherein said first memory means includes a digital read only memory or appropriately partitioned random access memory, and said second memory means includes a digital random access memory.

11. A real time biological performance evaluation and metered dose training device which comprises:

means for measuring normal resting respiratory air flow and generating a flow signal representative of said air flow;

means for integrating said air flow signal with relation to a time base and generating a volumetric signal representative of the integrated air flow;

means for detecting a predetermined lung exhalation volume and initiating an ideal volumetric respiration pattern concurrently with a prompt signal;

manually actuated means for introducing a metered dose of aerosol material into inspiration airflow;

means for comparing the volumetric signal with the ideal volumetric respiration pattern; and means for visually displaying the volumetric signal and ideal pattern in visually discernible superimposed observation modes on a dynamic display.

12. A device according to claim 11 further comprising means for presetting performance error limits and providing visual and auditory performance deficiency signals.

13. A device according to claim 11 further comprising means for displaying on the ideal respiration pattern a blinking dot in a predetermined time domain to precisely prompt the subject performance.

14. The device according to claim 11 further comprising means for activating auditory and visual alarms in response to predetermined deviation of the volumetric signal from the ideal pattern.

15. The device according to claim 11 comprising means for adjusting positive and negative error limits and means for detecting and indicating volumetric signals in relation to time parameters outside said error limits.

16. Inhalation therapy apparatus for enhancing patient performance during inhalation of aerosol treatment materials comprising:
    airflow conduit means for receiving inspiration and expiration air from the patient;
    manually actuated means for introducing a metered dose of aerosol material into the airflow conduit means;
    means for generating a first signal representative of airflow;
    means for indicating a cyclic expiration point representative of lung exhaustion;
    dosage signal means for indicating to the patient beginning of an inspiration cycle and substantially simultaneous manual activation of said manually activated means; and
    means for indicating completion of air intake in said inspiration cycle and manual actuation of said manually actuated means.

* * * * *